United States Patent
Keller et al.

(10) Patent No.: US 7,361,494 B1
(45) Date of Patent: Apr. 22, 2008

(54) TETRAHYDROPYRIMIDINE DIOXYGENASE GENE, POLYPEPTIDES ENCODED BY SAID GENE AND METHOD FOR PRODUCING THE SAME

(75) Inventors: Ullrich Keller, Berlin (DE); Nicolas Grammel, Berlin (DE)

(73) Assignee: Merck Patent GmbH, Darmstadt (DE)

( * ) Notice: Subject to any disclaimer, the term of this patent is extended or adjusted under 35 U.S.C. 154(b) by 257 days.

(21) Appl. No.: 10/130,932

(22) PCT Filed: Nov. 17, 2000

(86) PCT No.: PCT/DE00/04036

§ 371 (c)(1),
(2), (4) Date: May 7, 2003

(87) PCT Pub. No.: WO01/38500

PCT Pub. Date: May 31, 2001

(30) Foreign Application Priority Data

Nov. 24, 1999 (DE) ................................ 199 57 470

(51) Int. Cl.
C12N 9/14 (2006.01)
C12N 1/12 (2006.01)
C12N 15/00 (2006.01)
C12N 5/00 (2006.01)
A01H 9/00 (2006.01)

(52) U.S. Cl. .................. 435/195; 435/183; 435/320.1; 435/252.1; 435/325; 435/410; 435/419; 536/23.1; 536/23.2; 800/295

(58) Field of Classification Search ................ 435/195, 435/183, 191, 370.1, 257.3, 325, 410, 419; 536/23.2; 538/23.1, 23.2; 530/350
See application file for complete search history.

(56) References Cited

FOREIGN PATENT DOCUMENTS

| DE | 693 20 075 T2 | 4/1999 |
| --- | --- | --- |
| EP | 0 440 373 A | 8/1991 |
| EP | 0 553 884 B1 | 8/1998 |
| WO | WO 94/13806 | 6/1994 |
| WO | WO 97/47271 A | 12/1997 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Vain et al., Theor. Appl. Genet., vol. 107, pp. 210-217, 2003.*
Bode et al., "Antibody-directed fibrinolysis: An antibody specific for both fibrin and tissue plasminogen activator." Journal of Biological Chemistry, 264(2): 944-948, 1989.
Groose-Hovest Ludger et al., "A recombinant bispecific single-chain antibody induces targeted, supra-agonistic CD28-stimulation and tumor cell killing." European Journal of Immunology, 33(5): 1334-1340, 2003.
Malin and Lapidot, "Induction of synthesis of tetrahydropyrimidine derivatives in *Streptomyces* strains and their effect on *Escherichia coli* in response to osmotic and heat stress." Journal of bacteriology, 178(2): 385-395, 1996.
Mori et al., Database Nageneseq Online!, Accession No. T47925, XP002166790, Jun. 18, 1997.
Schoonjans et al., Fab chains as an efficient heterodimerization scaffold for the production of recombinant bispecific and trispecific antibody derivatives. Journal of Immunology, 165(12): 7050-7057, 2000.
Zamri et al., "A stereocontrolled synthesis of a new class of 3,4,5,6-tetrahydropyrimidine-based chiral amino acids." Tetrahedron et al., 55(16): 5157-5170, 1999.

* cited by examiner

*Primary Examiner*—Richard Hutson
(74) *Attorney, Agent, or Firm*—Foley & Lardner, LLP

(57) ABSTRACT

The present invention relates to enzymes having tetrahydropyrimidine dioxygenase activity, to the genes coding therefor, to the homologous and heterologous expression of these genes, to processes for preparing enzymes having tetrahydropyrimidine dioxygenase activity and the use of these enzymes for in vivo and in vitro production of hydroxylated tetrahydropyrimidine. In addition, the invention relates to the biotechnological use of the hydroxylated tetrahydropyrimidine prepared by one of the processes of the invention.

13 Claims, 5 Drawing Sheets

Fig. 3

```
peptide Ke15P6:    V   L   F   D   G   E   L   F   P   E   E   T....
170498A:                   ttc gac ggc gag ctg ttc ccg gag gag acc peptide Ke15P6:    .....E   E   T   H   L   P   E   V   L   Y   R
170498B:                gag gag acc cac ctg ccg gag gtc ctg tac
```

TETRAHYDROPYRIMIDINE DIOXYGENASE GENE, POLYPEPTIDES ENCODED BY SAID GENE AND METHOD FOR PRODUCING THE SAME

The present invention relates to enzymes having tetrahydropyrimidine dioxygenase activity, to the genes coding therefor, to the homologous and heterologous expression of these genes, to processes for preparing enzymes having tetrahydropyrimidine dioxygenase activity and the use of these enzymes for in vivo and in vitro production of hydroxylated tetrahydropyrimidine. In addition, the invention relates to the biotechnological use of the hydroxylated tetrahydropyrimidine prepared by one of the processes of the invention.

Figure 1:
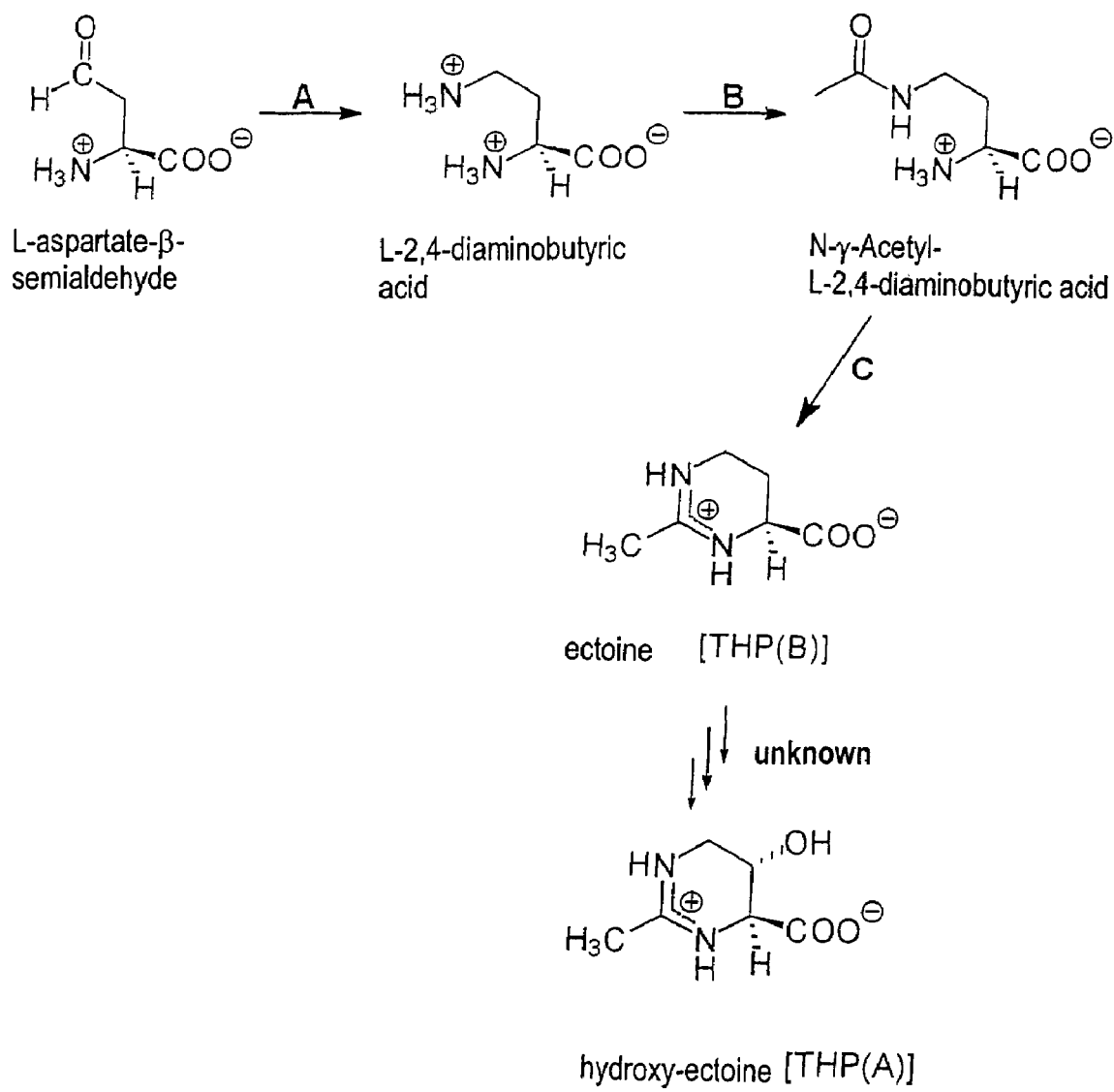

Following osmotic stress, microorganisms produce low molecular weight intracellular compounds which are referred to as osmolytes and which include the tetrahydropyrimidines. The tetrahydropyrimidines THP(B) (2-methyl-4-carboxy-3,4,5,6-tetrahydropyrimidine) and THP(A) (2-methyl-4-carboxy-5-hydroxy-3,4,5,6-tetrahydropyrimidine) are produced by various microorganisms as intracellular components of the cytoplasm [Ventosa, A. et al. (1998). Biology of moderately halophilic aerobic bacteria. *Microbiol. Mol. Biol. Rev.* 62, 504-544] (FIG. 1). These microorganisms include the halophilic eubacteria, actinomycetes, *bacillus* species and brevibacteria. The THPs can be isolated from these organisms in pure form and be employed in various forms in biotechnology, such as, for example, in the stabilization of proteins both in solution and on freeze drying thereof [Lippert, K. and Galinski, E. A. (1992). Enzyme stabilization by ectoine-type compatible solutes: protection against heating, freezing and drying. *Appl. Microbiol. Biotechnol.* 37, 61-65.], in influencing the interactions of proteins and nucleic acids [Lapidot, A. et al. (1995). Tetrahydropyrimidine derivatives inhibit binding of a Tat-like, arginine-containing peptide, to HIV TAR RNA in vitro. *FEBS Lett.* 367, 33-38; Malin, G. and Lapidot, A (1996). Induction of synthesis of tetrahydropyrimidine derivatives in *Streptomyces* strains and their effect on *Escherichia coli* in response to osmotic and heat stress. *J. Bacteriol.* 178, 385-395; Malin, G. et al. (1999). Effect of tetrahydropyrimidine derivatives on protein-nucleic acids interaction. Type 11 restriction endonucleases as a model system. *J. Biol. Chem.* 274, 6920-6929.] and in the refolding of denaturated proteins. In addition, an increased salt and heat tolerance can be found on addition of THP(A) or THP(B) to culture media of various prokaryotes such as, for example, *E. coli* [Malin, G. and Lapidot, A. (1996). Induction of synthesis of tetrahydropyrimidine derivatives in *Streptomyces* strains and their effect on *Escherichia coli* in response to osmotic and heat stress. *J. Bacteriol.* 178, 385-395.].

The characterized THP(A) biosynthetic pathway, shown in FIG. 1 starts from L-aspartate-β-semialdehyde. In the subsequent transamination reaction, L-2,4-diamino-butyrate transaminase catalyzes the formation of L-2,4-diaminobutyrate (DABA). The subsequent N-acetylation of DABA is effected by L-2,4-diaminobutyrate acetyltransferase using acetyl-coenzyme A. The intramolecular condensation reaction catalyzed by N-acetyl-γ-L,2,4-diaminobutyrate cyclase results in THP(B) [Peters, P. et al. (1990). The biosynthesis of ectoine. *FEMS Microbiol. Lett.* 71, 157-162; Ono, H. et al. (1999). Characterization of biosynthetic enzymes for ectoine as a compatible solute in a moderately halophilic eubacterium, *Halomonas elongata. J. Bacteriol.* 181, 91-99.]. By contrast, the steps to the biosynthesis of the 5-hydroxy derivative of THP(B), (THP(A)), are still unexplained.

Preparation of THPs by the processes known in the art is confined to the elaborate extraction of these compounds from the cells or culture filtrates from bacteria which produce THP(A) and/or THP(B). These processes are particularly cost-intensive because of the high salt concentrations in the culture medium.

Although a chemical synthesis of THPs is possible, this synthesis comprises a large number of synthetic steps and the use of an elaborate protective group technique, so that this complex process cannot be carried out economically, especially on a large scale. This particularly relates to the synthesis of THP(A) because the respective precursors cannot be obtained by chemical routes, and the consequence is additional difficulty for the chemical synthesis of THP(A).

The object of the invention is therefore to provide an improved process for preparing hydroxylated THPs, in particular THP(A).

The object of the invention is achieved by providing a process using a polypeptide having a tetrahydropyrimidine dioxygenase activity.

One aspect of the invention therefore relates to the nucleic acid sequences which code for polypeptides which have a tetrahydropyrimidine dioxygenase activity. These nucleic acid sequences comprise both DNA and RNA nucleic acid sequences and are selected from the following group of nucleic acid sequences:

(a) DNA nucleic acid sequence having the nucleotide sequence depicted in SEQ ID No.: 1;

(b) DNA nucleic acid sequence derived as a result of the degeneracy of the genetic code from the nucleotide sequence depicted in SEQ ID No.: 1;

(c) DNA nucleic acid sequence which hybridizes with at least one DNA nucleic acid sequence which has a DNA nucleic acid sequence according to (a) or (b);

(d) DNA nucleic acid sequence which is fragments, allelic or other variants of the DNA nucleic acid sequence having the nucleotide sequence depicted in SEQ ID No.: 1;

(e) RNA nucleic acid sequence derived from the DNA nucleic acid sequence according to (a) to (d); and (f) nucleic acid sequence having a degree of homology with one of the sequences according to (a) to (e) of more than 60%.

DNA nucleic acid sequences coding for polypeptides having tetrahydropyrimidine dioxygenase activity mean both genomic DNA nucleic acid sequences and cDNA nucleic acid sequences. The degree of homology of the nucleic acid sequence according to (f) with one of the sequences according to (a) to (e) is at least 60%, preferably 80% and particularly preferably more than 90%.

A further aspect of the present invention relates to polypeptides which have tetrahydropyrimidine dioxygenase activity and which are preferably encoded by one of the nucleic acid sequences according to (a), (b), (c), (d), (e) or (f). Particular preference is given to a polypeptide (SEQ ID No.: 6) which is encoded by the DNA nucleic acid sequence shown in SEQ ID No.: 1.

In another aspect, the present invention relates to DNA or RNA nucleic acid sequences according to (a), (b), (c), (d), (e) or (f) which have been isolated from an archaebacterium, a prokaryote or a eukaryote. Particular preference is given to such nucleic acid sequences when they have been isolated from a halophilic *eubacterium*, an *actinomycete*, a *bacillus* or a *brevibacterium*.

Preference is likewise given to nucleic acid constructs which comprise an operative unit which consists of a promoter sequence and a nucleic acid sequence according to (a), (b), (c), (d), (e) or (f).

Preference is likewise given to nucleic acid constructs which comprise an operative unit which consists of a promoter sequence and a nucleic acid sequence according to (a), (b), (c), (d), (e) or (f), and additionally comprise a nucleic acid sequence which codes for one or more secretion signals.

In a further aspect, the present invention relates to replicative recombinant vectors which comprise a nucleic acid sequence according to (a), (b), (c), (d), (e) or (f).

The invention further relates to cells which comprise a vector which undergoes autonomous replication in the cell and which comprises a nucleic acid sequence according to (a), (b), (c), (d), (e) or (f). Particular preference is given in this connection to bacteria cells, yeast cells or plant cells.

Preferred cells have a nucleic acid sequence according to (a), (b) (c), (d), (e) or (f) integrated into the genome by non-natural recombination. Particular preference is given in this connection to cells in which the non-natural recombination is into the genome of a bacterial cell, of a yeast cell or of a plant cell.

In an alternative aspect, the present invention relates to the use of an oligonucleotide as nucleic acid probes for identifying genes, where the nucleotide sequence of the oligonucleotide has been derived from that of the nucleic acid sequences according to (a), (b), (c), (d), (e) or (f), and the oligonucleotides are used for identifying chromosomal or extrachromosomal genes which are present in archaebacteria, prokaryotes or eukaryotes and which code for a polypeptide which has tetrahydropyrimidine dioxygenase activity.

The invention also relates to a plant which has been transformed with a recombinant DNA which comprises a DNA sequence as claimed in any of claims 1 to 4. Such a plant is distinguished by increased osmotic tolerance.

The invention further relates to a process for preparing a polypeptide having tetrahydropyrimidine dioxygenase activity, entailing cultivation of cells which comprise a nucleic acid section having a nucleic acid sequence according to (a), (b), (c), (d), (e) or (f) or a nucleic acid construct of the type explained above, in isolation of the polypeptide having tetrahydropyrimidine dioxygenase activity.

The method used for isolation of the polypeptide will depend, in a manner known to the skilled worker, on whether the cells used for the preparation comprise a nucleic acid section having a nucleic acid sequence according to (a), (b), (c), (d), (e) or (f) or a nucleic acid construct of the type explained above. With the first possibility, the prepared polypeptide can be isolated only after preceding disruption of the cells, and with the second possibility, in which the cells comprise a nucleic acid construct comprising a secretion signal, it would be possible to isolate the prepared polypeptide directly from the culture medium.

Another aspect of the invention relates to the use of a polypeptide having tetrahydropyrimidine dioxygenase activity for preparing hydroxylated tetrahydropyrimidine.

The preparation preferably takes place with the aid of a polypeptide having tetrahydropyrimidine dioxygenase activity in a living cell, the living cell being a bacterial cell, a yeast cell or a plant cell. The living cell containing the polypeptide having tetrahydropyrimidine dioxygenase activity may be present in a culture medium which contains tetrahydropyrimidine. In such a case, the living cell should be permeabilized, preferably before the preparation, in order to favor contact between the polypeptide having tetrahydropyrimidine dioxygenase activity and the tetrahydropyrimidine.

A preferred embodiment of the invention is described below, although this is not intended to be understood in such a way that a restriction of the protection desired by the inventor can be inferred therefrom.

Figure 2:
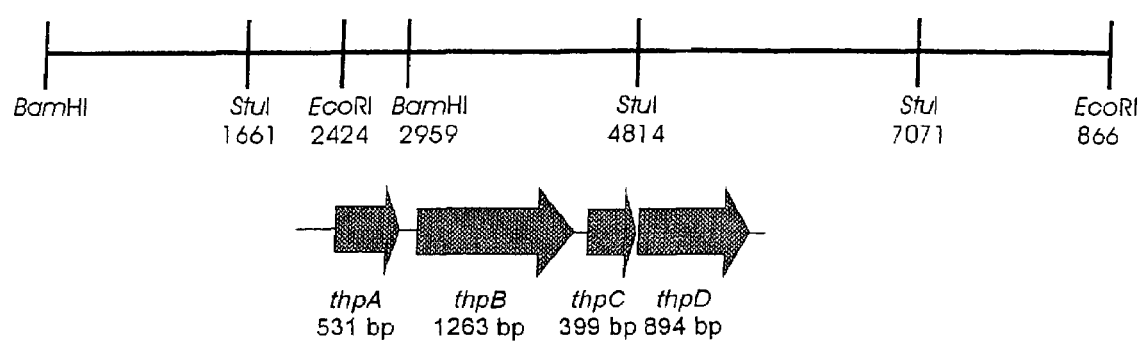

In order to find THP biosynthesis genes in *Streptomyces chrysomallus*, L-2,4-diaminobutyrate acetyltransferase, an enzyme of THP biosynthesis from *Streptomyces chrysomallus*, was purified. Oligonucleotide sequences were derived from tryptic peptide sequences of the L-2,4-diaminobutyrate acetyltransferase and employed for screening a cosmid bank. The gene of L-2,4-diaminobutyrate acetyltransferase and flanking regions were sequenced. Four open reading frames were found inter alia on the BamHI/EcoRI fragment, 8.7 kb in size. These genes, which code for THP biosynthesis enzymes, are referred to hereinafter as thpA, thpB, thpC and thpD (FIG. 2). The open reading frame referred to as thpD codes for an enzyme which has a THP(B) dioxygenase activity and a molecular weight of 32.7 kDa. This enzyme is an α-ketoglutarate-dependent dioxygenase which catalyzes the irreversible hydroxylation of THP(B) to THP(A). The thpD gene was expressed in *E. coli* and *Streptomyces*, and the corresponding protein (THP(D)) was purified by methods known in the art.

Use of the homologously or heterologously expressed THP(D) protein makes in vitro production of THP(A) possible. Complete hydroxylation of THP(B) to THP(A) is observed by incubation of the THP(D) protein in the presence of THP(B), α-ketoglutarate, ascorbic acid, iron(II) sulfate and catalase.

The gene which codes for the tetrahydropyrimidine dioxygenase is located on a BamHI/EcoRI fragment 8.7 kb in size. Expression of the *Streptomyces chrysomallus* genes present on this DNA fragment in microorganisms makes it possible to synthesize hydroxylated tetrahydropyrimidine.

Expression of the thpD gene in microorganisms which produced THP(B) makes in vivo production of the 5-hydroxy derivative of tetrahydropyrimidine (THP(A)) possible.

This process can be applied to a large number of microorganisms such as, for example, actinomycetes, bacilli or halophilic bacteria, as long as they have nucleic acid sequences which code for polypeptides having THP dioxygenase activity. With this proviso it is possible for the expression additionally to be carried out in any other prokaryotic or eukaryotic expression system.

The invention is explained in more detail below by means of examples.

EXAMPLE 1

Detection of L-2,4-diaminobutyrate acetyltransferase from *Streptomyces chrysomallus*

A nucleotide sequence was derived from an internal peptide sequence of the L-2,4-diaminobutyrate acetyltransferase previously purified from *Streptomyces chrysomallus* (FIG. 3). This nucleotide sequence was radiolabelled and employed as probe for screening a cosmid bank. Parts of the corresponding cosmid were subcloned and sequenced. Four open reading frames inter alia were found thereby, with thpA coding for L-diaminobutyrate acetyltransferase, thpB coding for L-aspartate-α-semialdehyde transaminase, thpC coding for N-acetyl-γ-L-2,4-diaminobutyrate cyclase and thpD coding for THP(B) dioxygenase (FIG. 2). Expression in other microorganisms is possible, in *Streptomyces lividans* serves as exemplary organism (see Example 2).

EXAMPLE 2

Expression of thpD in *Streptomyces lividans*

Figure 5:
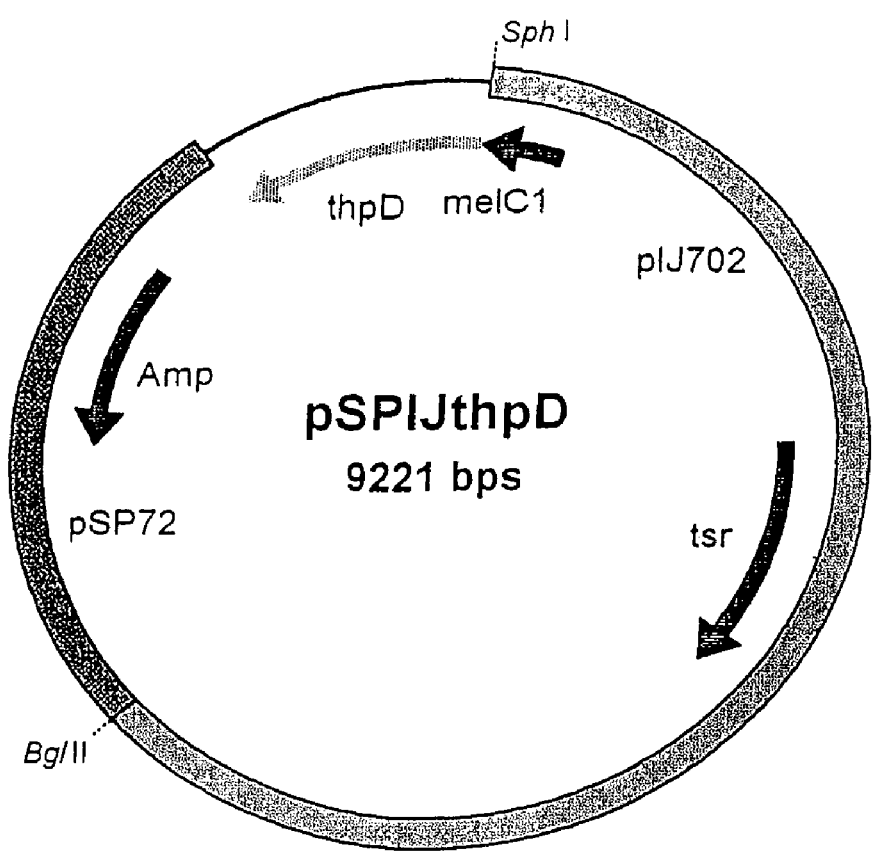

For expression of thpD in *Streptomyces lividans*, the thpD gene was cloned as SphI/HindIII fragment into the expression vector pSPIJ002 (FIG. 5). The resulting expression plasmid was called pSPIJthpD. The SphI and HindIII restriction cleavage sites were introduced by PCR mutagenesis (35 cycles; 1 min 95° C.; 90 sec 55° C.; 65 sec 72° C.; see Table 1 for primers). The plasmid pQE30thpD served as template for the PCR. This plasmid is a pQE30 derivative which contains the thpD gene as BamHI/HindIII PCR fragment (35 cycles; 1 min 95° C.; 90 sec 55° C.; 65 sec 72° C.; see Tab. 1 for primers). The primers used as shown in Table 1 as SEQ ID No.: 2-5. Ligation and transformation took place by standard methods.

EXAMPLE 3

Purification of hexa-His-THP(D) from *Streptomyces lividans*

YEME medium (34.0 g/l sucrose, 10 g/l glucose, 3 g/l yeast extract, 3 g/l malt extract, 5 g/l Bacto peptone and 0.2% $MgCl_2$) was inoculated to an $OD_{600}$ of 0.05 from a preculture of the *Streptomyces lividans* strain (transformed with pSPIJthpD, see Example 2) and incubated at 28° C. in a shaker. The cells were harvested after 72 hours. The cells were resuspended in disruption buffer (100 mM phosphate buffer pH 8.0, 10% glycerol, 1 mM benzamidine, 1 mM PMSF, 10 mM imidazole and 300 mM NaCl) and disrupted by passing through a French press cell (16 000 psi; equivalent to $1.105 \times 10^8$ Pa) twice. The cell-free crude extract was centrifuged in an SS34 rotor at 12 000 rpm for 30 min. The cell-free supernatant was chromatographed on an Ni-NTA matrix. The hexa-His-THP(D) protein elutes in the region of 30-100 mM imidazole.

EXAMPLE 4

In vitro synthesis of 2-methyl-4-carboxy-5-hydroxy-3,4,5,6-tetrahydropyrimidine (THP(A))

THP(B) dioxygenase activity is determined using the following reaction mixture:

| | |
|---|---|
| Potassium phosphate buffer, pH 8, | 10 mM |
| THP (B) | 5 mM |
| α-Ketoglutarate | 5 mM |
| Ascorbic acid | 5 mM |
| Iron (II) sulfate | 1 mM |
| Hexa-His-THP (D) variable in a total volume of | 100 μl. |

Figure 4:
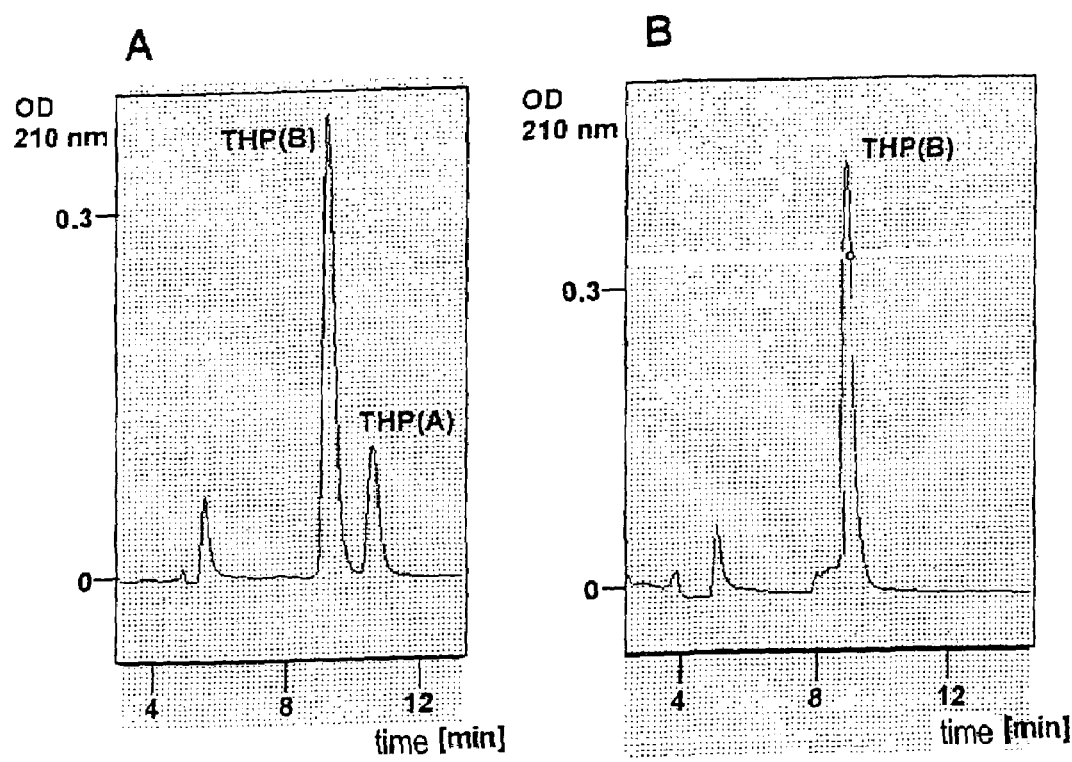

Incubation takes place at 30° C. for one hour. The product is analyzed by chromatography on an $NH_2$-Nucleosil HPLC column. Elution took place with 70% acetonitrile/$H_2O$. The elution profile is depicted in FIG. 4. Complete hydroxylation of THP(B) to THP(A) can be achieved with use of catalase (bovine liver, from Sigma).

FIG. 1: Biosynthesis of THP(B) starting from L-aspartate β-semialdehyde. A: L-2,4-diaminobutyrate transaminase, B: L-2,4-diaminobutyrate acetyltransferase, C: N-acetyl-diaminobutyric acid cyclase.

FIG. 2: Restriction map of the sequenced region and the location of the THP biosynthesis genes found. The corresponding base position is indicated under the restriction enzymes.

FIG. 3: Internal tryptic peptide sequence of the DABA acetyltransferase from *Streptomyces chrysomallus* and oligonucleotide sequence derived therefrom (170498A and 170498B). The encoding DNA sequence and amino acid sequence shown for 170498A is SEQ ID No: 7 and SEQ ID No: 9, respectively. The encoding DNA sequence and amino acid sequence shown for 170498B is SEQ ID No: 8 and SEQ ID No: 10, respectively.

FIG. 4: HPLC of THP(A) and THP(B) on an $NH_2$-Nucleosil column. In each case 1/10 of the reaction mixture which contained 5 mM THP(B), 5 mM a-ketoglutarate, 5 mM ascorbic acid, 1 mM $FeSO_4$ and 2 mg/ml THP(D) fusion protein (A) or buffer D (B) was loaded. Elution took place with 70% acetonitrile at a flow rate of 1 ml/min.

FIG. 5: pSPIJ002: shuttle vector produced by ligation of pSP72 (BglII) and pIJ702 (BglII). This expression vector can be used both in *E. coli* and in *Streptomyces*.

Tab. 1: PCR primers used for constructing plasmid pQE30thpD and pSPIJthpD.

PQE30thpD

FTHPD (30-mer):

5'-GCC TGA GGA TCC ATG ACC ACC GAA GTA CGC-3'

(SEQ ID NO.: 2)

RTHPD (27-mer):

5'-CCC GCC CGT GAA GCT TGC TAC TTC ACC-3'

(SEQ ID NO.: 3)

PSPIJthpD

FSPIJthp (30-mer):

5'-GAG GAG GAA TTC AGC ATG CGA GGA TCG CAT-3'

(SEQ ID No.: 4)

RSPIJthp (25-mer):

5'-AGT CCA AGC TCA GCT AAT TAA GCT T-3'

(SEQ ID No.: 5)

The invention claimed is:

1. An isolated nucleic acid that encodes a polypeptide having tetrahydropyrimidine dioxygenase activity, wherein said nucleic acid is a DNA nucleic acid having the nucleotide sequence depicted as SEQ ID NO: 1.

2. The nucleic acid of claim 1, wherein the nucleic acid has been isolated from an archaebacterium, a prokaryote cell or a eukaryote cell.

3. The nucleic acid of claim 2, wherein the nucleic acid has been isolated from a halophilic *eubacterium*, an *actinomycete*, a *bacillus* or a *brevibacterium*.

4. A nucleic acid construct, wherein the construct comprises in an operative unit a promoter sequence and the nucleic acid of claim 1.

5. The nucleic acid construct of claim 4, wherein the construct further comprises a nucleic acid sequence which codes for one or more secretion signals.

6. An isolated polypeptide encoded by the nucleic acid of claim 1 wherein said polypeptide has tetrahydropyrimidine dioxygenase activity.

7. A replicative recombinant vector comprising the nucleic acid of claim 1 or the nucleic acid construct of claim 4.

8. An isolated cell comprising the replicative recombinant vector of claim 7.

9. An isolated cell having a genome, wherein the nucleic acid of claim 1 is integrated into the genome by non-natural recombination.

10. The cell of any one of claims 8 or 9, wherein the cell is a bacterial cell, a yeast cell or a plant cell.

11. A plant transformed with a recombinant DNA comprising the nucleic acid of claim 1.

12. A method of preparing a polypeptide having tetrahydropyrimidine dioxygenase activity, comprising:

providing a cell according to claim 8, wherein the cell produces a polypeptide having tetrahydropyrimidine dioxygenase activity;

cultivating the cell in a medium; and isolating the polypeptide from the cell.

13. The method of claim 12 wherein the cell has been permeabilized, and wherein tetrahydropyrimidine is present in the culture medium.

* * * * *

SEQUENCE LISTING

<160> NUMBER OF SEQ ID NOS: 10

<210> SEQ ID NO 1
<211> LENGTH: 978
<212> TYPE: DNA
<213> ORGANISM: Streptomyces chrysomallus

<400> SEQUENCE: 1

```
cccccgtca cgggacggga ggaccatgac gagaacggtg tctacccact gctgaccgag      60
gaggcctgaa ccaccatgac caccgaagta cgcgccgatc tgtaccccte gcgcggcgcc    120
gccgagatga ccactccccg ccaggacccg gtcatctggt ccgcgccggg cgcaccgggt    180
ccggtcgccg ccaaggacct ccagggatac gagcacgacg gcttcctcac cgtcgaccag    240
ctcatcgccc cggacgaggt cgccgtctac caggcggagc tgaaccggct gatctccgac    300
ccggcggtcc gcgccgacga gcgctcgatc gtcgagaagc agtcgcagaa cgtacggtcc    360
gtcttcgagg tccaccggat cagcgaggtc ttcgccggtc tggtccgcga cgagcgggtg    420
gtgggccggg cccgccagat cctcggctcg gacgtgtacg tccaccagtc ccggatcaac    480
gtgaagccgg gcttcggggc cacgggcttc tactggcact cggacttcga gacctggcac    540
gcggaggacg gtctgccgaa catgcggacg gtgtccgtgt cgatcgcgct gaccgagaac    600
ttcgacacca acggcgggct gatgatcatg cccggttcgc acaagacgtt cctcggctgc    660
gcgggcgaga cgccgaagga caactacaag aagtcgctcc agatgcagga cgccggcacc    720
ccgtccgacg aggcgctgac gaagatggcc gaccgccacg gcatcaggct cttcacgggc    780
agggccggtt cggcgacctg gttcgactgc aacgccatgc acggctcggg cgacaacatc    840
accccgtacg cgcgcagcaa cgtcttcatc gtcttcaaca gcgtggagaa cgcggcccag    900
gagcccttcg cggctccgat ccgccgcccc gagttcatcg gggcgcggga cttcaccccg    960
gtgaagtagc gggccgca                                                  978
```

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
gcctgaggat ccatgaccac cgaagtacgc                                      30
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
cccgcccgtg aagcttgcta cttcacc                                         27
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 4
gaggaggaat tcagcatgcg aggatcgcat                                              30

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agtccaagct cagctaatta agctt                                                   25

<210> SEQ ID NO 6
<211> LENGTH: 297
<212> TYPE: PRT
<213> ORGANISM: Streptomyces chrysomallus

<400> SEQUENCE: 6
```

Met Thr Thr Glu Val Arg Ala Asp Leu Tyr Pro Ser Arg Gly Ala Ala
 1               5                  10                  15

Glu Met Thr Thr Pro Arg Gln Asp Pro Val Ile Trp Ser Ala Pro Gly
            20                  25                  30

Ala Pro Gly Pro Val Ala Ala Lys Asp Leu Gln Gly Tyr Glu His Asp
        35                  40                  45

Gly Phe Leu Thr Val Asp Gln Leu Ile Ala Pro Asp Glu Val Ala Val
    50                  55                  60

Tyr Gln Ala Glu Leu Asn Arg Leu Ile Ser Asp Pro Ala Val Arg Ala
65                  70                  75                  80

Asp Glu Arg Ser Ile Val Glu Lys Gln Ser Gln Asn Val Arg Ser Val
                85                  90                  95

Phe Glu Val His Arg Ile Ser Glu Val Phe Ala Glu Leu Val Arg Asp
            100                 105                 110

Glu Arg Val Val Gly Arg Ala Arg Gln Ile Leu Gly Ser Asp Val Tyr
        115                 120                 125

Val His Gln Ser Arg Ile Asn Val Lys Pro Gly Phe Gly Ala Thr Gly
    130                 135                 140

Phe Tyr Trp His Ser Asp Phe Glu Thr Trp His Ala Glu Asp Gly Leu
145                 150                 155                 160

Pro Asn Met Arg Thr Val Ser Val Ser Ile Ala Leu Thr Glu Asn Phe
                165                 170                 175

Asp Thr Asn Gly Gly Leu Met Ile Met Pro Gly Ser His Lys Thr Phe
            180                 185                 190

Leu Gly Cys Ala Gly Glu Thr Pro Lys Asp Asn Tyr Lys Lys Ser Leu
        195                 200                 205

Gln Met Gln Asp Ala Gly Thr Pro Ser Asp Glu Ala Leu Thr Lys Met
    210                 215                 220

Ala Asp Arg His Gly Ile Arg Leu Phe Thr Gly Arg Ala Gly Ser Ala
225                 230                 235                 240

Thr Trp Phe Asp Cys Asn Ala Met His Gly Ser Gly Asp Asn Ile Thr
                245                 250                 255

Pro Tyr Ala Arg Ser Asn Val Phe Ile Val Phe Asn Ser Val Glu Asn
            260                 265                 270

Ala Ala Gln Glu Pro Phe Ala Ala Pro Ile Arg Arg Pro Glu Phe Ile

-continued

```
                275                 280                 285
Gly Ala Arg Asp Phe Thr Pro Val Lys
    290                 295

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ttcgacggcg agctgttccc ggaggagacc                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gaggagaccc acctgccgga ggtcctgtac                                      30

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Phe Asp Gly Glu Leu Phe Pro Glu Glu Thr
  1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Glu Thr His Leu Pro Glu Val Leu Tyr Arg
  1               5                  10
```